United States Patent
Geng et al.

(10) Patent No.: US 10,563,196 B2
(45) Date of Patent: Feb. 18, 2020

(54) PRIMER FOR NUCLEIC ACID RANDOM FRAGMENTATION AND NUCLEIC ACID RANDOM FRAGMENTATION METHOD

(71) Applicant: BGI SHENZHEN, Shenzhen (CN)

(72) Inventors: Chunyu Geng, Shenzhen (CN); Hongyan Han, Shenzhen (CN); Guangying Guo, Shenzhen (CN); Wenwei Zhang, Shenzhen (CN); Hui Jiang, Shenzhen (CN); Yuan Jiang, Shenzhen (CN)

(73) Assignee: MGI TECH CO., LTD, Shenzhen, Guangdong (CN)

( * ) Notice: Subject to any disclaimer, the term of this patent is extended or adjusted under 35 U.S.C. 154(b) by 350 days.

(21) Appl. No.: 15/519,530

(22) PCT Filed: Oct. 17, 2014

(86) PCT No.: PCT/CN2014/088809
§ 371 (c)(1),
(2) Date: Apr. 14, 2017

(87) PCT Pub. No.: WO2016/058173
PCT Pub. Date: Apr. 21, 2016

(65) Prior Publication Data
US 2017/0275616 A1    Sep. 28, 2017

(51) Int. Cl.
*C12N 15/10* (2006.01)
*C12Q 1/6806* (2018.01)
*C12Q 1/68* (2018.01)
*C12Q 1/6853* (2018.01)
*C12Q 1/686* (2018.01)
*C40B 40/08* (2006.01)
*C40B 50/06* (2006.01)

(52) U.S. Cl.
CPC ......... *C12N 15/1093* (2013.01); *C12N 15/10* (2013.01); *C12Q 1/68* (2013.01); *C12Q 1/686* (2013.01); *C12Q 1/6806* (2013.01); *C12Q 1/6853* (2013.01); *C40B 40/08* (2013.01); *C40B 50/06* (2013.01)

(58) Field of Classification Search
CPC .................................................. C12N 15/1093
USPC .............................................................. 506/9
See application file for complete search history.

(56) References Cited

U.S. PATENT DOCUMENTS

| | | |
|---|---|---|
| 2004/0209299 A1 | 10/2004 | Pinter et al. |
| 2011/0281736 A1 | 11/2011 | Drmanac et al. |
| 2014/0274729 A1 | 9/2014 | Kurn et al. |

FOREIGN PATENT DOCUMENTS

| | | | |
|---|---|---|---|
| CN | 102703426 A | 10/2012 | |
| WO | 2004081183 A2 | 9/2004 | |
| WO | WO-2013017861 A2 * | 2/2013 | ........... C12Q 1/6855 |
| WO | 2014150931 A1 | 9/2014 | |

OTHER PUBLICATIONS

International Search Report for PCT/CN2014/088809 dated Jul. 24, 2015 and its English translation provided by WIPO.
Written Opinion of the International Search Authority for PCT/CN2014/088809 dated Jul. 24, 2015 and its English translation provided by WIPO.

* cited by examiner

*Primary Examiner* — Karla A Dines
(74) *Attorney, Agent, or Firm* — Ladas & Parry, LLP

(57) ABSTRACT

The present invention provides a primer for nucleic acid random fragmentation and a nucleic acid random fragmentation method. The primer consists of a plurality of upstream random primers and downstream random primers. The sequence composition of the upstream random primers is 5'-X-Y-3', and the sequence composition of the downstream random primers is 5'-P-Y'-X'-close-3', wherein Y and Y' are random sequences, X is all or part of sequences of a sequencing platform 5' end adaptor, X' is all or part of sequences of a sequencing platform 3' end adaptor, P is phosphorylation modification, and close is close modification. The primer of the present invention adopts double random anchoring of both the upstream random primers and the downstream random primers, and a DNA sample can be randomly broken.

13 Claims, 2 Drawing Sheets
Specification includes a Sequence Listing.

PRIMER FOR NUCLEIC ACID RANDOM FRAGMENTATION AND NUCLEIC ACID RANDOM FRAGMENTATION METHOD

CROSS REFERENCE TO RELATED APPLICATION

The present application is the U.S. national phase of PCT Application PCT/CN2014/088809 filed on Oct. 17, 2014, the disclosure of which is incorporated herein by reference in its entirety.

TECHNICAL FIELD

The present application relates to the field of nucleic acid disruption, particularly relates to primers for nucleic acid random fragmentation and a nucleic acid random fragmentation method based on the primers.

BACKGROUND OF THE INVENTION

Ever since Ronaghi invented pyrosequencing method, opening up the era of second generation sequencing, up to now the second generation sequencing has been experiencing a phase of rapid development. However, with the advances in high-throughput sequencing, the aspect of high-throughput and low-cost sample preparation is becoming a key factor of great concern. Sample treatment methods and automatic apparatuses based on various principles have been continually developed, which mainly include sample fragmentation, terminal treatment of nucleic acid molecules, and adaptor ligation, etc.

Sample fragmentation is mainly achieved by physical methods such as ultrasonic cleaving, or enzymatic methods such as non-specific endonuclease treatment. The physical method predominantly used involves a Covaris disruptor based on proprietary Adaptive Focused Acoustics (AFA) technology, whereby geometrically focused acoustic energy is utilized under isothermal condition. Acoustic energy having a wavelength of 1 mm is focused to a sample by a spherical solid-state ultrasonic transducer of >400 kHz. The method ensures the maintenance of the completeness of nucleic acid samples and achieves a high recovery rate. The Covaris disruptor includes the economical M series, the single-tube full-power S series and the higher throughput E and L series. The fragments obtained from the physical method exhibit a good fragment randomness. However, a number of Covaris disruptors are needed for the sake of throughput, and subsequent separate operations of terminal processing, adaptor ligation, PCR and various purifications are also required. One of the enzymatic methods involves NEB Next dsDNA Fragmentase available from NEB. The reagent first introduces random nick positions into double-stranded DNA, then recognizes the nick positions and cleaves the complementary DNA strands with another enzyme, thus achieving the aim of disrupting the DNA. Such a reagent can be used in genome DNA, whole genome amplification products, PCR products etc. and provides good randomness. Nevertheless, it will generate some artificial short fragment insertions and deletions, and also inevitably entails subsequent separate operations of terminal processing, adaptor ligation, PCR and corresponding purifications. Additionally, the transposase disruption kits available from Epicentra, as represented by Nextera kit, utilize transposase to achieve DNA fragmentation and adaptor addition at the same time, thus reducing the length of time for sample processing.

Considering the convenience of various operations, the transposase disruption method is undoubtedly much better than other methods in terms of throughput and convenience in operation. Nevertheless, such a disruption method has its own disadvantage as follows. The transposase relies on a specific 19 bp Me sequence to achieve transposition. Therefore, although the transposase can embed two completely different adaptor sequences and thus add the different adaptor sequences respectively to the 5'-end and the 3'-end of a target sequence, both adaptors need to comprise a specific Me sequence. One of the resulting influences is that the fragments generated from disruption will have, symmetrically, a Me sequence on both terminal ends. Also, there will be a gap of 9 nt base deletion between the sequence of interest or the sequence obtained from disruption and the Me sequence, due to the special effect of the transposase. Identical Me sequences franking the target sequence may affect some of the downstream applications. For example, with respect to the second generation sequencing technology based on ligation process, the Me sequences flanking the same strand are complementary sequences, which would easily result in annealing within the single-stranded molecule and is thus unfavorable for the binding of the anchoring primers.

Chinese patent application CN 102703426 A proposes a method to address this issue, in which the sequences obtained following disruption are subjected to digestion with a specific endonuclease to remove the 9 nt sequence and the Me sequence. This method only takes advantage of transposase disruption to randomly disrupt a nucleic acid sequence, but introduces the drawback that subsequently adaptors need to be added separately. Also, the method suffers from excessive steps and is not adapted to applications of higher throughput.

SUMMARY OF THE INVENTION

An object of the present application is to provide novel primers for nucleic acid random fragmentation. On this basis, another object of the present application is to provide a novel method for disrupting a DNA with random primers, that is, a nucleic acid random fragmentation method.

In order to achieve the above objects, the present application provides the technical solutions outlined below.

In one aspect, the present application discloses primers from nucleic acid random fragmentation. The primers consist of a plurality of upstream random primers and a plurality of downstream random primers, the sequence composition of the upstream random primers being 5'-X-Y-3', and the sequence composition of the downstream random primers being 5'-P-Y'-X'-close-3', wherein Y and Y' are a random sequence, X is the whole or part of the sequence of the 5'-end adaptor for a sequencing platform, X' is the whole or part of the sequence of the 3'-end adaptor for a sequencing platform, P is phosphorylation modification, and close is a blocking modification used to prevent the formation of 3-5 phosphodiester linkage.

It should be noted that the upstream random primers and the downstream random primers of the present application are different from common PCR primers. By design, the upstream random primers and the downstream random primers hybridize and bind to the same template strand. Moreover, in the extension stage, extension only occurs between the upstream random primer and the downstream random primer that are most adjacent to each other in a way that the upstream random primer extends towards the 3'-end such that the inbetween of the upstream random primer and the downstream random primer is filled. As the 5'-end of the downstream random primer has phosphorylation modification, the 3'-end of the extended sequence of the upstream random primer can be linked with the 5'-end of the downstream random primer. That is, the upstream random primer, together with its extended sequence, is linked with the downstream random primer into a single sequence. As both the upstream random primers and the downstream random primers hybridize to the template in a random manner, random disruption of a DNA sample can be achieved. What is different from amplification of a DNA sample with conventional random primers is that, of the primers of the present application, only the upstream random primers will extend, and will immediately stop extending upon reaching the downstream random primers. In contrast, amplification of a DNA sample with conventional random primers would result that, following the second round of amplification, one upstream primer extended strand may correspond to a plurality of downstream primers, such that a series of discrete bands are amplified, affecting the accuracy of the results.

It should also be noted that the Y and Y' random sequences in the present application, like the sequences of conventional random primers, consist of 3-12 bases, preferably 5-9 bases. The X and X' sequences are adaptor sequences for a sequencing platform, prepared for subsequent sequencing. X is the whole or part of the sequence of the 5'-end adaptor for a sequencing platform. The reason for this is as follows. After a DNA sample is randomly disrupted, the DNA random fragments purified need to be amplified with a pair of universal primers for amplification, that is, PCR amplification. During PCR amplification with the primers using the DNA random fragments as templates, the whole sequence of the 5'-end adaptor can be completed by virtue of the design of the primers. Therefore, the X sequence in the upstream random primers can be the whole or part of the sequence of the 5'-end adaptor for a sequencing platform. Based on the same consideration, X' is the whole or part of the sequence of the 3'-end adaptor for a sequencing platform.

Preferably, the blocking modification is dideoxy modification. It should be noted that the blocking modification serves to prevent the 3'-end of the downstream random primers from extending and also prevent the ligation of the downstream random primers with each other. Therefore, theoretically, any blocking modification that can prevent the formation of 3-5 phosphodiester linkage can be employed in the present application. After extensive consideration, the present applicant confirmed that dideoxy modification plays the role of blocking without affecting the hybridization of the random primers.

Preferably, the 5'-end of the X sequence of the upstream random primers further comprises 2-6 protecting bases; and the 3'-end of the X' sequence of the downstream random primers further comprises 2-6 protecting bases, and the blocking modification is on the terminal protecting base.

It should be noted that the protecting bases serve to stabilize the sequence. It is thus appreciated that in less preferred embodiments, the protecting groups can be absent.

Preferably, the upstream random primers comprise a plurality of intervening bases between the X sequence and the Y sequence; and the downstream random primers comprise a plurality of intervening bases between the Y' sequence and the X' sequence. It should be noted that the intervening bases are not necessary. While the intervening bases also serve to ensure the stability of the sequence, they would be amplified in the subsequent PCR amplification following the purification operation, that is, they would result in a spacing between the adaptor and the DNA fragments obtained from random disruption. Therefore, it would be best not to add intervening bases, unless specially required.

In an embodiment of the present application, the X sequence of the upstream random primers has the sequence as shown in SEQ ID NO. 1, and the X' sequence of the downstream random primers has the sequence as shown in SEQ ID NO. 2:

```
SEQ ID No. 1:
5'-GACCGCTTGGCCTCCGACT-3'

SEQ ID No. 2:
5'-GTCTCCAGTCGAAGCCCGA-3'.
```

In another aspect, the present application discloses a nucleic acid random fragmentation method, which comprises anchoring double random primers of the present application to a DNA sample. Specifically, the method comprises hybridizing the upstream random primers and the downstream random primers to a denatured DNA sample; filling the sequence between the upstream random primer and the downstream random primer which are most adjacent to each other by extending the 3'-end of the upstream random primer under the action of a DNA polymerase; and ligating the 3'-end of the extended sequence of the upstream random primer to the 5'-end of the downstream random primer under the action of a DNA ligase, that is, the upstream random primer, together with its extended sequence, being linked with the downstream random primer into a single sequence. Thus, double random disruption of the DNA sample is achieved through the random hybridization of the upstream random primers and the downstream random primers.

It should be noted that the method of the present application achieves extension and ligation reactions by adding certain amounts of the upstream random primers and the downstream random primers and the denatured DNA sample into a reaction liquid which comprises a DNA polymerase, a DNA ligases and dNTPs. In fact, the hybridization of the upstream random primers and the downstream random primers and the extension of the upstream random primers in the present application follow the same principle as does a conventional PCR. The random primers first hybridize to a denatured DNA sample, and then the 3'-end of the upstream random primers begins to extend under the action of a DNA polymerase. As only the downstream random primers have phosphorylation modification at the 5'-end, therefore following extension only the upstream random primer and the downstream random primer which are most adjacent to each other can be linked by a DNA ligase into a single sequence. This ensures the accuracy of random disruption and prevents the introduction of a wrong structure.

Preferably, in the process of hybridization of the upstream random primers and the downstream random primers to the denatured DNA sample, the total usage amount of the upstream random primers and the downstream random primers is R×n picomoles, wherein $2.7 \leq R \leq 750$, $n=1.515 \times (m \div L)$, m is the weight of the DNA sample in ng, L is the expected DNA fragment length after disruption, and n is the theoretical usage amount in picomoles of the upstream random primers and the downstream random primers required to disrupt the DNA sample into fragments having a length of L.

It should be noted that the usage amount of the upstream random primers and the downstream random primers is dependent on the degree of fragmentation desired. It is appreciated that the larger the usage amount of the upstream random primers and the downstream random primers, the more densely the random primers hybridize to the DNA molecular strand, hence the shorter the distance between the upstream random primer and the downstream random primer which are most adjacent to each other, and thus the smaller the single sequence obtained from linking, that is, the smaller the DNA fragments obtained, or in other words, the higher the degree of fragmentation; otherwise, the DNA fragments obtained from random fragmentation is larger. The present applicant deduced that the usage amount of the primers required to disrupt a DNA sample into fragments having a length of L is theoretically n, and concluded based on extensive trials and analyses that, depending on the different disruption lengths L desired, the total usage amount of the upstream random primers and the downstream random primers is practically R times the theoretical usage amount n, that is, R×n picomoles. The larger the R, the smaller the L of the fragments obtained from disruption, wherein L is the number, in bp, of the base pairs in the fragments obtained from disruption.

Preferably, the ratio of the molar usage amount of the upstream random primers to that of the downstream random primers is 1-3:1, preferably 2:1, and preferably, R=20.

In yet another aspect, the present application discloses a method for constructing a nucleic acid library, comprising subjecting a DNA sample to random fragmentation by using the nucleic acid random fragmentation method of the present application, then subjecting the DNA fragments obtained from double random disruption to PCR amplification with a pair of universal primers to enrich the random fragments and obtain a nucleic acid library, wherein the universal primers consist of a forward primer and a reverse primer, the 3'-end of the forward primer having the whole or part of the sequence of the 5'-end adaptor for a sequencing platform, and the 3'-end of the reverse primer having the whole or part of the reverse complementary sequence of the 3'-end adaptor for a sequencing platform.

It should be noted that the forward primer and the reverse primer as a primer set in the present application are conventional PCR amplification primers designed for the DNA fragments obtained from random disruption. PCR amplification is conducted with the primers using the DNA fragments obtained from random fragmentation as templates, so as to achieve signal amplification of the DNA fragments obtained from random fragmentation. Therefore, the 3'-end of the forward primer has the whole or part of the sequence of the 5'-end adaptor for a sequencing platform, and the 3'-end of the reverse primer has the whole or part of the reverse complementary sequence of the 3'-end adaptor for a sequencing platform. The upstream random primers and the downstream random primers may comprise the whole or part of the sequence of the adaptor, and the forward primer and the reverse primer may also comprise the whole or part of the sequence, so long as the products from PCR amplification comprise all of the adaptor sequences. By way of example, this is explained with respect to the upstream random primers and the forward primer only. When the X sequence of the upstream random primers is the whole sequence of the 5'-end adaptor for a sequencing platform, the 3'-end of the forward primer can be the whole sequence of the 5'-end adaptor or part of the sequence of the 5'-end adaptor, so long as the forward primer can hybridize to the X sequence of the upstream random primers to amplify the complete 5'-end adaptor sequence. Likewise, when the X sequence of the upstream random primers is part of the sequence of the 5'-end adaptor for a sequencing platform, the sequence of the 5'-end adaptor can be completed by the forward primer. In this case, the 3'-end of the forward primer can be the whole sequence of the 5'-end adaptor, or can be the completing sequence and part of the sequence that hybridizes to the 5'-end adaptor sequence in the X sequence of the upstream random primers, thus amplifying the complete 5'-end adaptor. Therefore, the 3'-end of the forward primer can be the whole or part of the sequence of the 5'-end adaptor for a sequencing platform; and likewise, the 3'-end of the reverse primer has the whole or part of the reverse complementary sequence of the 3'-end adaptor for a sequencing platform.

It should further be noted that although the primers of the present application could ensure random disruption of a DNA sample very well and would not generate interference associated with discrete fragments, the copy number of the random DNA fragments is limited, because when linking the upstream random primer and the downstream random primer, PCR amplification is essentially not conducted and only the upstream random primers are extended. Therefore, for sequencing or library construction, the DNA fragments obtained from random disruption need to be PCR amplified using the forward primer and the reverse primer. Moreover, both the forward primer and the reverse primer are designed according to the adaptors for a sequencing platform, that is, all of the random DNA fragments actually comprise the whole or part of the sequence of the adaptors for a sequencing platform. When the adaptor sequences for a sequencing platform are determined, the forward primer and the reverse primer would amplify all of the DNA fragments, hence referred to as universal primers. It should further be noted that, in general, after linking the random disrupted DNA fragments, the fragments linked need to be purified prior to PCR amplification. Conventional DNA purification methods can be used to purify the randomly disrupted DNA fragments linked. In the present application, the magnetic bead method is preferably used to separate and purify the DNA fragments.

Preferably, the forward primer and the reverse primer respectively have, at the 5'-end, an adaptor sequence for a second sequencing platform.

It should be noted that it is not necessary that the forward primer and the reverse primer should respectively have at the 5'-end an adaptor sequence for a second sequencing platform. It is appreciated that if sequencing only needs to be conducted on one sequencing platform, then only the 5'-end adaptor and the 3'-end adaptor for the sequencing platform are needed. The adaptors for the second sequencing platform are for the sake of convenience of subsequent sequencing.

In an embodiment of the present application, the forward primer comprises the sequence as shown in SEQ ID NO. 1, and the reverse primer comprises the sequence as shown in SEQ ID NO. 3:

```
SEQ ID No. 3:
5'-TCGGGCTTCGACTGGAGAC-3'.
```

By adopting the above-described technical solutions, the present application has the advantageous effects as follows:

The primers and the nucleic acid random fragmentation method based on the primes according to the present application are suitable for the random disruption of various DNA samples, including cDNA sequences. The upstream and downstream double random primers can cover almost the whole sequence of the target sequence and achieve a high coverage uniformity, providing a better basis for subsequent molecular biology operations and information mining. Moreover, the random disruption method of the present application allows to accomplish the whole process of sample treatment by using only a few conventional tool enzymes and PCR nucleic acid amplification apparatus, making it possible for medium and small-sized research institutes, colleges and universities and downstream application sectors to independently conduct high-throughput library preparation. Additionally, the present application has the advantages of being convenient and fast because it only involves denaturation of the target sequence, random anchorage of the random primers, and polymerization and ligation reactions prior to subsequent amplification, allowing to get rid of the dependence on large-scale high-end apparatus and equipment or expensive kits. The characteristics of simpleness and ease to operation of the present application allow to greatly decrease the requirement for the professional skills of technicians and substantially expand the fields of application of large-scale high-throughput sequencing.

DETAILED DESCRIPTION OF THE INVENTION

Figure 1:
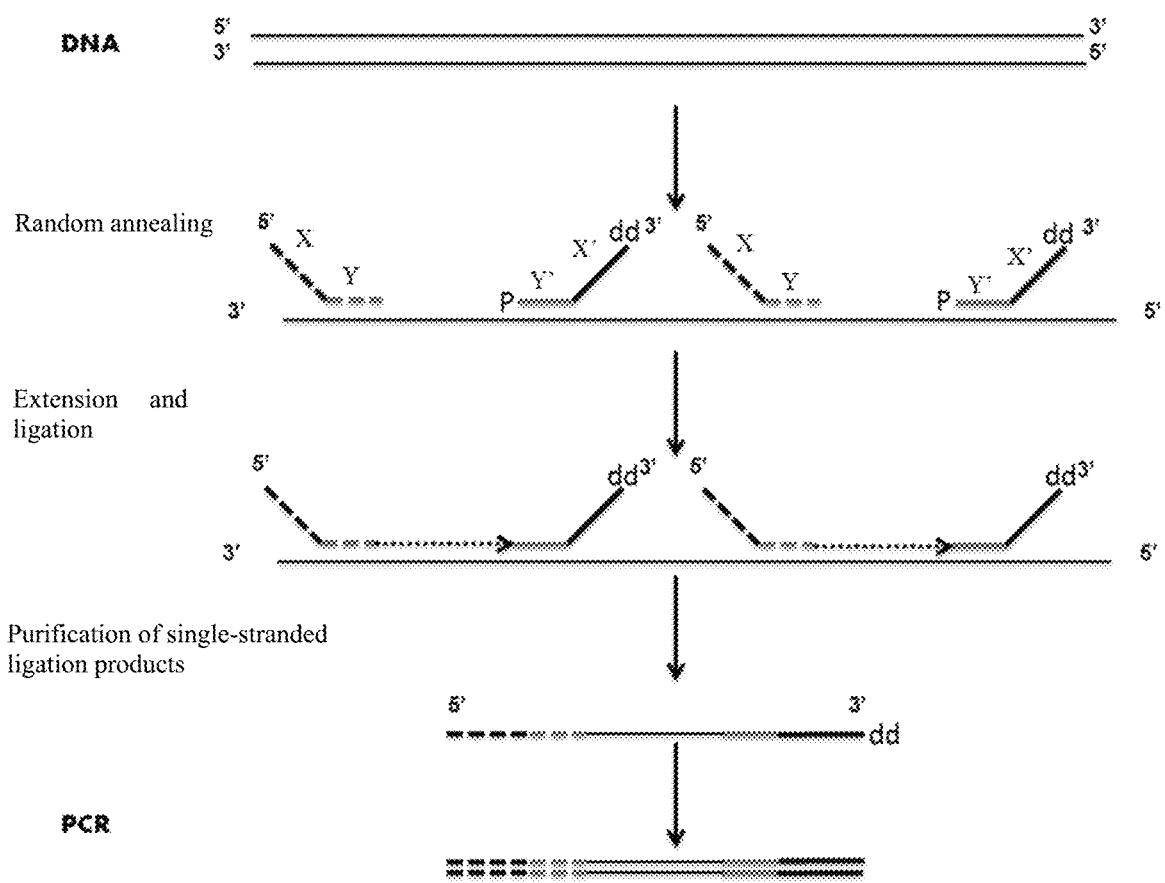
FIG. 1 is a schematic depiction of the DNA random disruption method in the example of the present application.

Primers are designed in the present application such that the upstream random primers and the downstream random primers bind to the same template strand rather than separately bind to two complementary template strands. The aim is not to conduct PCR amplification. Rather, as shown in FIG. 1, the spacing between the upstream random primer and the downstream random primer that are adjacent to each other is filled by virtue of the extension of the upstream random primer, and the primers are linked by a DNA polymerase into a complete single sequence. As both the upstream primers and the downstream primers are random, double random disruption of a DNA sample can be achieved. And, as the upstream random primers will stop extending upon reaching the downstream random primers, the problem associated with amplification of a DNA sample with conventional random primers could be avoid. Said problem is that one upstream primer extended strand may correspond to a plurality of downstream primers following the second round of amplification, resulting in discrete bands and affecting subsequent operations.

The nucleic acid random fragmentation method based on the primers of the present application takes a short time and is accomplished almost singly in a PCR instrument, enabling to achieve the fastest sample preparation. The method allows for automatic operations and can effectively reduce faulty human operation and decrease systematic error in sample preparation in comparison to other methods. Moreover, the method allows to get rid of the dependence on large-scale high-end apparatus and equipment or expensive kits.

It should be noted that in the nucleic acid random fragmentation method of the present application, the upstream random primers and the downstream random primers are hybridized to a denatured DNA sample, wherein the denaturation of the DNA sample can be achieved by using high temperature treatment method or chemical reagent denaturation method. The duration of high temperature treatment is inversely proportional to the temperature, that is, the higher the temperature, the shorter the treatment duration. Suitable denaturation temperatures are in the range of 98-95° C. for a treatment duration of 1-5 minutes. In an embodiment of the present invention, a temperature of 95° C. for a treatment duration of 5 minutes is selected. For chemical reagent denaturation method, common denaturing reagents include KOH, NaOH and EDTA, etc., and are not specifically limited in the present application. After chemical reagent denaturation, for the annealing reaction to proceed, the alkali ions in the reaction system should be neutralized, such that the reaction system is maintained in a neutral, suitable salt ion environment. The neutralization buffer solution can be various low concentration acid buffer solutions, and only the alkali solution treatment group is treated with the neutralization buffer solution, such as the combined buffer solution of HCl and Tris-HCl.

The fragment size of the extension products can be designed to meet the requirement of a sequencing platform by regulating the molar ratios of the upstream random primers to the downstream random primers to the templates, which is not specifically limited herein. In the present application, the number of the random sequences in the upstream random primers and the downstream random primers can be designed to vary, with the random sequences comprising 5 random bases, 6 random bases, 7 random bases, 8 random bases, etc., so as to ensure that the primers bind to different positions of the target sequence. This is the same as with conventional random primers and will not be specifically limited herein. Moreover, in order to prevent the upstream random primers and the downstream random primers from introducing a wrong structure during subsequent reactions, the 5'-end of the upstream random primers is designed to be without phosphorylization modification, while the 5'-end of the downstream random primers is designed to have phosphorylization modification, and the 3'-end of the downstream random primers is designed to have blocking modification, preferably dideoxy modification, so as to prevent the formation of 3-5 phosphodiester linkage. Additionally, the upstream random primers and the downstream random primers can comprise adaptor sequences suitable for subsequent use with different sequencing platforms.

Additionally, the DNA polymerase can be selected from conventional DNA polymerases, and the ligase used following extension can also be selected from conventional DNA ligases, which is not specifically limited herein. In an embodiment of the present application, after ligation, the single-stranded DNA can be purified by single-stranded DNA magnetic bead selection method, the concentration of the magnetic beads being 1.0 fold. PCR amplification is conducted using the single-stranded DNA as template to achieve signal amplification of the DNA fragments obtained from random disruption.

In the present application, the usage amount of the upstream random primers and the downstream random primers directly affects the length of the DNA fragments obtained from disruption. Therefore, in preferred embodiments of the present application, the upstream random primers and the downstream random primers are added to a DNA sample in a total usage amount of R×n picomoles, wherein $2.7 \leq R \leq 750$, $n=1.515 \times (m \div L)$, m is the weight of the DNA sample in ng, and L is the expected DNA fragment length after disruption. In the above formula, n=1.515×(m÷L) was theoretically deduced by the present applicant, while the range of the value of R was derived according to the requirement for different fragment sizes after disruption and based on extensive trials and analyses, the larger the value of R, the smaller the fragments. The process of deducing n=1.515×(m÷L) is as follows:

Taking 3G human genome as an example, the genome comprises 3×10⁹ base pairs and has a mass molar concentration of about M=(3×10⁹×660) g/mol=(3×10⁶×660) ng/pmol=1.98×10⁹ ng/pmol, genomic DNA with a mass of m (ng) has a mole number of $n_1 = m \div M = m/(3 \times 10^6 \times 660 \times 10^{12})$ mol, genomic DNA with a mass of m (ng) has a molecule number of $N_1 = n_1 \times Na = m \div M \times Na$, disruption into molecules with a length of L (bp) theoretically needs a random primer molecule number of $n_2 = (3 \times 10^9 \div L) \times N_1$, and disruption into molecules with a length of L (bp) theoretically needs a random primer mole number of $n = n_2 \div Na$, therefore, $$n = n_2 \div Na = (3 \times 10^9 \div L) \times N_1 \div Na =$$
$$(3 \times 10^9 \div L) \times (m \div M \times Na) \div Na = 3 \times 10^9 \times m \div L \div M =$$
$$(3 \times 10^9 \div 1.98 \times 10^9) \times m \div L = 1.515 \times m \div L \text{ pmol},$$

wherein Na is Avogadro's number, $Na = 6.02 \times 10^{23}$.

That is, theoretically, n picomoles of upstream random primers and downstream random primers are needed in order to disrupt m nanograms of 3G human genome into fragments with a length of L. Practically however, according to extensive trials and analyses, R times the total amount of the upstream random primers and the downstream random primers of n picomoles, i.e., R×n picomoles, need to be added in order to obtain fragments with a length of L, the smaller the L, the larger the R.

It should be noted that, according to the formula deduced, the theoretical usage amount n of the upstream random primers and the downstream random primers theoretically has no direct relationship with the actual length of the DNA sample. It is the length L of the fragments desired to be obtained from disruption and the total weight of the DNA sample that directly affect n. Therefore, the formula for the theoretical usage amount n deduced by taking 3G human genome as an example in the present application is not to be limited to 3G human genome only. In other words, the nucleic acid random fragmentation method and the library construction method according to the present application find wide applicability and can be used to treat any DNA samples, including cDNA.

It should further be noted that the theoretical usage amount n in the present application is deduced based on double-stranded DNA, and that a DNA sample obtained from a trial is generally also double-stranded DNA. Therefore, the deduction and the definition of the usage amount of the upstream random primers and the downstream random primers of the present application find wide applicability. It is appreciated that for some special single-stranded DNA samples, the above deduction applies, except that the corresponding mass molar concentration M is substituted. The mass molar concentration of single-stranded DNA is about M=Y×324.5 g/mol, wherein Y is the length of the single-stranded DNA. As the samples to be obtained are generally double-stranded DNA, the case of single-stranded DNA is not specifically defined in the present application.

The present application is described in further detail with reference to a specific example and accompanying drawings. The following example only serves to further describe the present application and is not to be construed as limiting the present application thereto.

Example

1. Primer Design

In this example, upstream random primers and downstream random primers comprising 8 random sequence sites were designed and ordered, the sequences being as follows:

upstream random primers:

5'-GAC<u>GACCGCTTGGCCTCCGACT</u>TNNNNNNNN-3', downstream random primers:

5'-P-NNNNNNNN<u>GTCTCCAGTCGAAGCCCGA</u>CG-ddC-3', wherein, in the upstream random primers, "GACCGCTTGGCCTCCGACT" is the 5'-end adaptor sequence for a sequencing platform of the X sequence, the "GAC" before the 5'-end adaptor represents protecting bases, "NNNNNNNN" is the random Y sequence, and a spacing base is present between the X sequence and the Y sequence; and in the downstream primers, "GTCTCCAGTCGAAGCCCGA" is the 3'-end adaptor sequence for a sequencing platform of the X' sequence, the "CG" after the 3'-end adaptor represents protecting bases, "NNNNNNNN" is the random Y' sequence, P is phosphorylation modification, and ddC is dideoxy modification. The random sequence was randomly synthesized, which is not specifically defined herein.

The synthesized primers were diluted to 10 µM for later use.

2. Denaturation of Genomic DNA Sequence

In this example, chemical denaturation method was employed. Specifically, the extracted human genomic DNA was diluted to 50 ng/µL. A denaturation reaction system was established according to the following systems: DNA sample 1 µl, ddH₂O 0.6 µl, denaturation buffer solution 1 µl, 2.6 µl in total. Then, reaction was allowed at room temperature for 3 minutes to accomplish denaturation. In this example, the denaturation buffer solution comprised 208 mM KOH and 1.3 mM EDTA.

3. Annealing of Random Primers

Into the above-said denaturation system was added 1 µl of neutralization buffer solution comprising 208 mM HCl and 312.5 mM Tris-HCl, and reaction was allowed at room temperature for 3 minutes. One (1) µl of annealing reaction solution was added, wherein the downstream random primers and the upstream random primers were added into the reaction solution in a ratio of 1:2, and the total concentration of the upstream random primers and the downstream random primers is 5.1 picomoles.

The annealing reaction solution was formulated as follows: 10× phi buffer 0.46 µl ddH₂O 0.03 µl, upstream random primers 10 µM 0.34 µl, downstream random primers 10 µM 0.17 µl, 1 µl in total. Reaction was allowed at room temperature for 10 minutes.

4. Sequence Extension

Into the above reaction system was added 15.4 µl of extension reaction solution, the concentration of dNTPs in the extension reaction solution being 0.85 nmol. The extension reaction solution was formulated as follows: 10×phi buffer 1.54 μl, pure water 3.56 μl, dimethyl sulfoxide 1 μl, 5M betaine 8 μl, 0.25 mM each of dNTP 0.85 μL, 2 U/μl DNA polymerase 0.25 μl, 400 U/μl DNA ligase 0.2 μl, 15.4 μl in total.

The conditions for extension were correlated to the size of the library suitable for a sequencing platform. In this example, extension at 37° C. for 20 minutes was employed, then reaction at 65° C. for 15 minutes was employed to thermally inactivate the DNA polymerase. It should be noted that as the size of the fragments obtained from random fragmentation is determined by the molar ratio of the total of the upstream random primers and the downstream random primers to the DNA sample, it is appreciated that the larger the fragments, the longer the extension duration in the extension conditions, otherwise the smaller the fragments, the shorter the extension duration. Therefore, the extension conditions are correlated to the size of the fragments and hence to the size of the library.

5. Purification of Ligation Products

The single-stranded ligation products were purified by magnetic bead method. In this example, 1.0 fold PEG32 magnetic beads were used. 30 μL of PEG32 magnetic beads were added into 30 μL of the ligation system described above to purify the single-stranded ligation products, which were then redissolved in pure water, thus obtaining randomly disrupted single-stranded DNA.

6. PCR Reaction

The purified randomly disrupted DNA was used as template for amplification, and a primer set was designed that was directed to the 5'-end adaptor and the 3'-end adaptor of the upstream random primers and the upstream random primers, the forward primer in the primer set being as shown in SEQ ID NO. 4, and the reverse primer being as shown in SEQ ID NO. 5.

```
SEQ ID No. 4:
5'-TCCTAAGACCGCTTGGCCTCCGACT-3',

Seq ID NO. 5:
5'-AGACAAGCTCGATCGGGCTTCGACTGGAGAC-3'.
```

It should be noted that compared with the forward primer of the sequence

"GACCGCTTGGCCTCCGACT"

as shown in SEQ ID NO. 1 and the reverse primer of the sequence

"TCGGGCTTCGACTGGAGAC"

as shown in SEQ ID NO. 3, the forward primer and the reverse primer in this example were respectively added at the 5'-end with an adaptor for a second sequencing platform, thus obtaining the forward primer and the reverse primer of SEQ ID NO. 4 and SEQ ID NO. 5 respectively. It is appreciated that the adaptor for a second sequencing platform added at the 5'-end would not affect amplification. Therefore, the forward primer and the reverse primer as shown in SEQ ID NO. 1 and SEQ ID NO. 3 respectively could also be used in this example.

PCR reaction system: purified single-stranded DNA 20.5 μl, 2×PCR buffer 25 μl, 20 μM forward primer 2 μl, 20 μM reverse primer 2 μl 400 M/μl DNA polymerase 0.5 μl, 50 μl in total.

PCR reaction conditions: denaturation at 95° C. for 3 min; then 15 cycles of 95° C. 30 sec, 55° C. 30 sec and 72° C. 1 min; then extension at 72° C. for 10 min; and at last standby at 4° C.

7. Sequencing and Verification

The PCR products were sequenced on an Illumina Hiseq2000 PE101. The reads obtained from sequencing were filtered and aligned to a reference genomic sequence. The aligned data size and the genome coverage at different depths were statistically calculated, the results being as shown in Table 1.

TABLE 1

Degree of coverage and distribution of uniformity of the sequenced data as aligned to a reference genome

| | |
|---|---|
| Raw reads (M) | 4.5 |
| Alignment percentage | 99.70% |
| Reads of unique alignment (M) | 4.5 |
| Genome coverage degree | 99.99% |
| Genome coverage degree at 4X depth | 99.89% |
| Genome coverage degree at 10X depth | 98.53% |
| Genome coverage degree at 20X depth | 96.25% |
| Genome coverage degree at 30X depth | 85.20% |
| Genome coverage degree at 40X depth | 73.55% |
| Genome coverage degree at 50X depth | 55.60% |

The alignment percentage indicates that the fragments obtained from double random primer amplification in this example were basically of the target species, suggesting that the specificity was good. The genome coverage degree indicates that the target genome was basically completely covered, suggesting that the random disruption method of this example had a good randomness; and the genome coverage degree at different depths indicates that the uniformity of coverage in this example was good, with most of the regions being deeply covered, such as 4×, 10×, which could meet the need for subsequent variation analysis.

Figure 2:
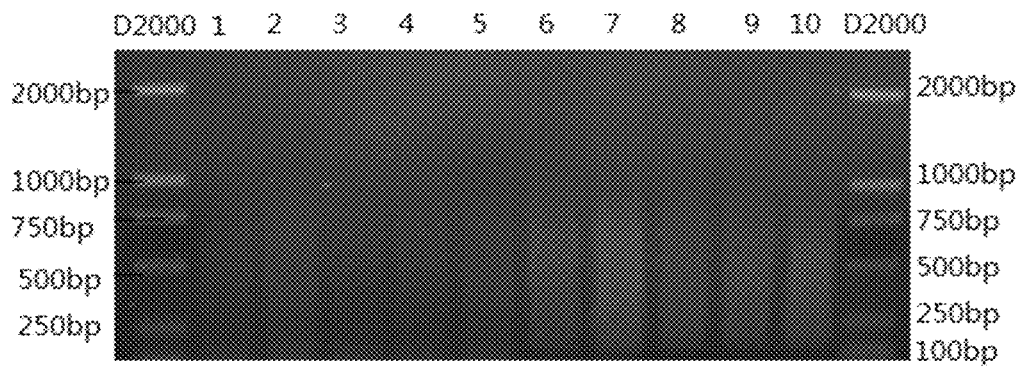
FIG. 2 is a diagram showing the result of electrophoresis with respect to condition optimization in the example of the present application.

On the basis of the above experiment, this example further optimized on the number of different random sequences, and the ratio of the usage amount of the upstream random primers to that of the downstream random primers. Moreover, a comparative experiment was conducted on three polymerases. The results are as shown in FIG. 2. In FIG. 2, lane D2000 represents the result of electrophoresis of DNA marker; lane 1 represents the result of electrophoresis of the case where the random base sequence consisted of 5 bases, the ratio of the downstream random primers:the upstream random primers=1:1, and Taq DNA polymerase was used; lane 2 represents the result of electrophoresis of the case where the random base sequence consisted of 5 bases, the ratio of the downstream random primers:the upstream random primers=2:1, and Taq DNA polymerase was used; lane 3 represents the result of electrophoresis of the case where the random base sequence consisted of 5 bases, the ratio of the downstream random primers:the upstream random primers=3:1, and Taq DNA polymerase was used; lane 4 represents the result of electrophoresis of the case where the random base sequence consisted of 5 bases, the ratio of the downstream random primers:the upstream random primers=3:1, and E. coli DNA polymerase I was used; lane 5 represents the result of electrophoresis of the case where the random base sequence consisted of 5 bases, the ratio of the downstream random primers:the upstream random primers=3:1, and Klenow Fragment was used; lane 6 represents the result of electrophoresis of the case where the random base sequence consisted of 9 bases, the ratio of the downstream random primers:the upstream random primers=2:1, and Klenow Fragment was used; lane 7 represents the result of electrophoresis of the case where the random base sequence consisted of 8 bases, the ratio of the downstream random primers:the upstream random primers=2:1, and Klenow Fragment was used; lane 8 represents the result of electrophoresis of the case where the random base sequence consisted of 5 bases, the ratio of the downstream random primers:the upstream random primers=2:1, and Klenow Fragment was used; lane 9 represents the result of electrophoresis of the case where the random base sequence consisted of 6 bases, the ratio of the downstream random primers:the upstream random primers=2:1, and Klenow Fragment was used; and lane 10 represents the result of electrophoresis of the case where the random base sequence consisted of 7 bases, the ratio of the downstream random primers:the upstream random primers=2:1, and Klenow Fragment was used. The results indicate that, with respect to the three polymerases compared, klenow fragment showed a better effect, with respect to the number of the random base sequences compared, 8 random bases showed a better effect in random anchored PCR, and with respect to the ratio of the downstream random primers to the upstream random primers, a ratio in the range of 1-3:1 was acceptable, although the ratio of 2:1 showed a better effect.

Figure 3:
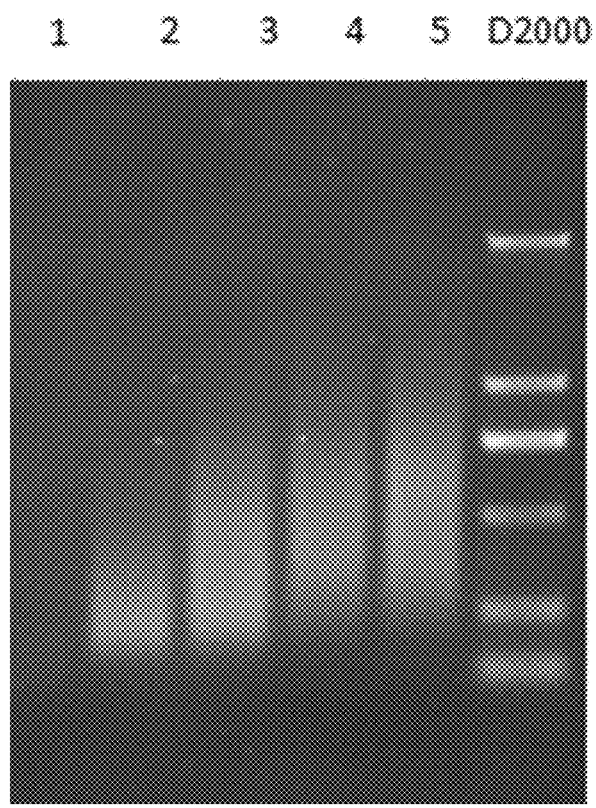
FIG. 3 is a diagram showing the result of electrophoresis with respect to condition optimization in the example of the present application.

On the basis of the above, this example further experimented on the total usage amount of the upstream random primers and downstream random primers, the results being as shown in FIG. 3. In FIG. 3, lane D2000 represents DNA marker; lane 1 represents negative control; lane 2 represents the result of electrophoresis of the case where downstream random primers:upstream random primers=2:1, the total amount of the random primers was 200 picomoles, and klenow Fragment was used; lane 3 represents the result of electrophoresis of the case where downstream random primers:upstream random primers=2:1, the total amount of the random primers was 51 picomoles, and klenow Fragment was used; lane 4 represents the result of electrophoresis of the case where downstream random primers:upstream random primers=2:1, the total amount of the random primers was 5.1 picomoles, and klenow Fragment was used; and lane 5 represents the result of electrophoresis of the case where downstream random primers:upstream random primers=2:1, the total amount of the random primers was 0.51 picomoles, and klenow Fragment was used. Results indicated that a total amount of the random primers of 5.1 picomoles showed the best effect. That is, it was calculated, based on the DNA sample m=50 ng and disruption into L=300 bp, that the theoretical primer usage amount n=0.253 picomole, and R=5.1/0.253, i.e., approximately 20. That is, the actual usage amount of the upstream random primers and downstream random primers required for disrupting 50 ng of the DNA sample into 300 bp was 20 times the theoretical usage amount. As to the value of R, extensive trials and studies were conducted in this example. The results of analyses and trials indicated that based on library construction, that is, based on the size of the fragments required for library construction, the range of the value of R was $2.7 \leq R \leq 750$, depending on the length L of disruption. The smaller the L, the higher the multiple of the actual usage amount over the theoretical usage amount, that is, the larger the R. R was preferably selected to be 20 for the conventional disruption of a DNA sample into 300 bp.

In this example, upstream random primers and downstream random primers were used to conduct double random anchoring to achieve random disruption of a DNA sample, then the purified randomly disrupted single-stranded DNA fragments were amplified using a primer set to obtain a DNA library suitable for use with different sequencing platforms. The operation was simple and convenient. This could avoid the dependence on special equipments and expensive kits and greatly expand the field of application of large-scale high-throughput sequencing.

The disclosure set forth hereinabove has described the present application in further detail by way of embodiments and examples, and is not to be construed as limiting the particular implementations of the present invention thereto. A number of simple deductions or substitutions could be made by a person of common skill in the art to which the present application belongs without departing from the concept of the present invention, and are deemed to fall within the scope of protection of the present application.

We claim:

1. Primers for nucleic acid random fragmentation, wherein: the primers consist of a plurality of upstream random primers and a plurality of downstream random primers, the sequence composition of the upstream random primers being 5'-X-Y-3', and the sequence composition of the downstream random primers being 5'-P-Y'-X'-close-3', wherein Y and Y' are a random sequence, X is the whole or part of the sequence of the 5'-end adaptor for a sequencing platform, X' is the whole or part of the sequence of the 3'-end adaptor for a sequencing platform, P is phosphorylation modification, and close is a blocking modification used to prevent the formation of a 3-5 phosphodiester linkage.

2. The primers according to claim 1, wherein: the blocking modification is a dideoxy modification.

3. The primers according to claim 1, wherein: the 5'-end of the X sequence of the upstream random primers further comprises 2-6 bases; and the 3'-end of the X' sequence of the downstream random primers further comprises 2-6 bases, and the blocking modification is on a terminal base.

4. The primers according to claim 1, wherein: the X has the sequence as shown in SEQ ID NO. 1, and the X' has the sequence as shown in SEQ ID NO.2:

SEQ ID NO. 1:
5'-GACCGCTTGGCCTCCGACT-3',

SEQ ID NO. 2:
5'-GTCTCCAGTCGAAGCCCGA-3'.

5. A nucleic acid random fragmentation method, which comprises anchoring double random primers of claim 1 to a DNA sample, and specifically comprises hybridizing the upstream random primers and the downstream random primers to a denatured DNA sample; filling the sequence between the upstream random primer and the downstream random primer which are most adjacent to each other by extending the 3'-end of the upstream random primer under the action of a DNA polymerase; and ligating the 3'-end of the extended sequence of the upstream random primer to the 5'-end of the downstream random primer under the action of a DNA ligase, that is, the upstream random primer together with its extended sequence being linked with the downstream random primer into a single sequence, thus achieving double random disruption of the DNA sample through the random hybridization of the upstream random primers and the downstream random primers.

6. The method according to claim 5, wherein: in the process of hybridization of the upstream random primers and the downstream random primers to the denatured DNA sample, the total usage amount of the upstream random primers and the downstream random primers is R×n picomoles, wherein $2.7 \leq R \leq 750$, $n=1.515 \times (m \div L)$, m is the weight of the DNA sample in ng, L is the expected DNA fragment length after disruption, and n is the theoretical usage amount in picomoles of the upstream random primers and the downstream random primers required to disrupt the DNA sample into fragments having a length of L.

7. The method according to claim 6, wherein: the ratio of the molar usage amount of the upstream random primers to that of the downstream random primers is 1-3:1.

8. The method according to claim 7, wherein: R=20.

9. The method according to claim 7, wherein: the ratio of the molar usage amount of the upstream random primers to that of the downstream random primers is 2:1.

10. The method according to claim 9, wherein: R=20.

11. A method for constructing a nucleic acid library, comprising subjecting a DNA sample to random fragmentation by using the method of claim 5, then subjecting the DNA fragments obtained from double random disruption to PCR amplification with a pair of universal primers to enrich the random fragments and obtain a nucleic acid library, wherein the universal primers consist of a forward primer and a reverse primer, the 3'-end of the forward primer having the whole or part of the sequence of the 5'-end adaptor for a sequencing platform, and the 3'-end of the reverse primer having the whole or part of the reverse complementary sequence of the 3'-end adaptor for a sequencing platform.

12. The method according to claim 11, wherein: the forward primer and the reverse primer respectively have, at the 5'-end, an adaptor sequence for a second sequencing platform.

13. The method according to claim 11, wherein: the forward primer comprises the sequence as shown in SEQ ID NO. 1, and the reverse primer comprises the sequence as shown in SEQ ID NO. 3:

```
SEQ ID NO. 3:
5'-TCGGGCTTCGACTGGAGAC-3'.
```

\* \* \* \* \*

SEQUENCE LISTING

```
<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 1
gaccgcttgg cctccgact                                                19

<210> SEQ ID NO 2
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 2
gtctccagtc gaagcccga                                                19
```

```
<210> SEQ ID NO 3
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 3
tcgggcttcg actggagac                                            19

<210> SEQ ID NO 4
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 4
tcctaagacc gcttggcctc cgact                                     25

<210> SEQ ID NO 5
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 5
agacaagctc gatcgggctt cgactggaga c                              31
```